Figure 1:
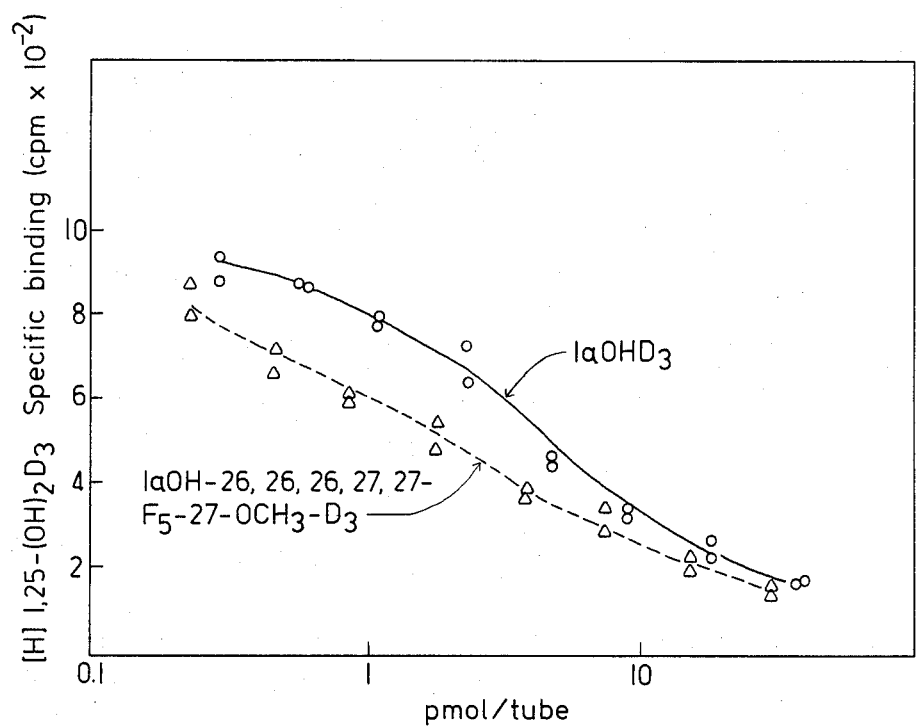

United States Patent [19]

DeLuca et al.

[11] Patent Number: 4,619,920
[45] Date of Patent: Oct. 28, 1986

[54] 26,26,26,27,27-PENTAFLUORO-1α-HYDROXY-27-METHOXYVITAMIN D$_3$

[75] Inventors: Hector F. DeLuca, Madison, Wis.; Nobuo Ikekawa; Yoshiro Kobayashi, both of Tokyo, Japan; Yoko Tanaka, Delmar, N.Y.

[73] Assignee: Wisconsin Alumni Research Foundation, Madison, Wis.

[21] Appl. No.: 776,342

[22] Filed: Sep. 16, 1985

[51] Int. Cl.$^4$ .............................................. C07J 9/00
[52] U.S. Cl. .................... 514/167; 260/397.2
[58] Field of Search .............. 260/397.2; 514/167

[56] References Cited

U.S. PATENT DOCUMENTS 4,358,406 11/1982 DeLuca et al. ............... 260/397.2
4,411,833 10/1983 DeLuca et al. ............... 260/397.2

Primary Examiner—Elbert L. Roberts
Attorney, Agent, or Firm—Howard W. Bremer

[57] ABSTRACT

The invention provides a new derivative of vitamin D$_3$, 26,26,26,27,27-pentafluoro-1α-hydroxy-27-methoxycholecalciferol and a process for preparing the same.

The compound is characterized by some vitamin D-like activity except that it exhibits negligible activity in mobilizing bone. This characteristic indicates that the compound would find ready application in the treatment of disease or physiological states which evince loss of bone mass and application in other situations where metabolic calcium imbalances are found.

8 Claims, 1 Drawing Figure

26,26,26,27,27-PENTAFLUORO-1α-HYDROXY-27-METHOXYVITAMIN D₃

This invention was made with Government support under NIH Grant No. AM 14881 awarded by the Department of Health and Human Services and NSF US/-Japan Cooperative Grant No. INT-8016902 awarded by the National Science Foundation. The Government has certain rights in this invention.

TECHNICAL FIELD

This invention relates to a compound which is characterized by vitamin D-like activity.

More specifically this invention relates to a derivative of vitamin $D_3$, to a method for preparing such compounds and to novel intermediates generated during such process.

Vitamin $D_3$ is a well-known agent for the control of calcium and phosphorous homeostasis. In the normal animal or human this compound is known to stimulate intestinal calcium transport and bone-calcium mobilization and is effective in preventing rickets.

It is also now well known that to be effective, vitamin $D_3$ must be converted in vivo to its hydroxylated forms. The vitamin is first hydroxylated in the liver to form 25-hydroxy-vitamin $D_3$ and is further hydroxylated in the kidney to produce 1α,25-dihydroxy-vitamin $D_3$ or 24,25-dihydroxyvitamin $D_3$. The 1α-hydroxylated form of the vitamin is generally considered to be the physiologically active or hormonal form of the vitamin and to be responsible for what are termed the vitamin D-like activities, such as increasing intestinal absorption of calcium and phosphate, mobilizing bone mineral, and retaining calcium in the kidneys.

BACKGROUND ART

Since the discovery of biologically active metabolites of vitamin D there has been much interest in the preparation of structural analogs of these metabolites, because such compounds may represent useful therapeutic agents for the treatment of diseases resulting from calcium metabolism disorders. A variety of vitamin D-like compounds have been synthesized. See, for example, U.S. Pat. Nos. 3,741,996 directed to 1α-hydroxycholecalciferol; 3,907,843 directed to 22-dehydro-25-hydroxycholecalciferol; 3,906,014 directed to 3-deoxy-1α-hydroxycholecalciferol; and 4,069,321 directed to the preparation of various side chain-fluorinated vitamin $D_3$ derivatives and side chain-fluorinated vitamin $D_3$ derivatives and side chain-fluorinated dihydrotachysterol analogs.

Certain fluoro derivatives of the accepted hormonal form of the vitamin, 1,25-dihydroxycholecalciferol (1,25-$(OH)_2D_3$) are of particular interest because they are characterized by at least as great if not greater activity than 1,25-$(OH)_2D_3$. These are, 24,24-difluoro-1,25-$(OH)_2D_3$ (U.S. Pat. No. 4,201,881) and 26,26,26,27,27,27-hexafluoro-1α,25-dihydroxycholecalciferol (U.S. Pat. No. 4,358,406).

Also of interest is the 26,26,26,27,27,27-hexafluoro derivative of 25-hydroxycholecalciferol (see U.S. Pat. No. 4,248,791) which exhibits greater vitamin D-like activity than 25-hydroxycholecalciferol.

DISCLOSURE OF THE INVENTION

A new derivative of vitamin $D_3$ has now been prepared.

The derivative has been identified as 26,26,26,27,27-pentafluoro-1α-hydroxy-27-methoxyvitamin $D_3$. The compound is characterized by properties which are unexpected for a vitamin $D_3$ derivative in that it exhibits little activity in in vivo bone resorption (as measured by serum calcium concentration) while being substantially more active than 1α-hydroxycholecalciferol (U.S. Pat. No. 3,741,996) in binding to receptor sites.

These unusual properties suggest that the compound would be eminently suitable in applications where it is desired to enhance new bone formation (mineralization) and to that end would be highly suitable for administration in conjunction or combination with vitamin D or a derivative thereof which displays traditional vitamin D-like activity, i.e. both bone resorption and bone mineralization. Disease states for which such conjunctive or combinative administration would be of particular value are those where there is a tendency toward or evidence of loss of bone mass, such as, for example, postmenopausal osteoporosis, senile osteoporosis and osteopenia. Analagously, disease states in animals which cause loss of bone mass or which are evidenced by inadequate bone mineralization such as, leg weakness condition in turkeys, chickens and poults or other domesticated animals would benefit from the administration of the compound of this invention either alone or in conjunction or combination with vitamin D or other vitamin D derivatives.

Also, the compound, because it evidences some vitamin D-like properties, would find application in the treatment of mineral (calcium and phosphous in particular) imbalance conditions as manifested, for example, in hypoparathyroidism, renal osteodystrophy, osteomalacia, etc. in man, in milk fever disease in dairy cattle and in the thinning of egg shells in fowl.

BEST MODE FOR CARRYING OUT THE INVENTION

The compounds of this invention can be readily synthesized in accordance with the following schematic and description. In the schematic and the description like compounds are identified by like numbers.

The oxalyl diester of 1α,3β-diacetoxychol-5-en-24-ol (Y. Kobayashi, T. Taguchi, S. Mitsuhashi, T. Eguchi, E. Oshima and N. Ikekawa, Chem., Pharm. Bull., 30, 4297 (1982)) was oxidized with dimethylsulfoxide to give the 24-aldehyde (1). Condensation with 2,2,4,4-tetratris(trifluoromethyl)-1,3-dithiethane provided the hexafluoro-24-ene (2) in good yield. The 24-double bond was reduced with sodium borohydride to give the hexafluorocholesterol derivative (3). The C-7 double bond was introduced with N-bromo succinimide as a usual procedure. When the diacetate was hydrolyzed with KOH-MeOH, one fluorine atom at C-27 position was replaced with a methoxy group to give the diene (4). This replacement was confirmed by the mass spectral data. The diene (4) was then subjected to

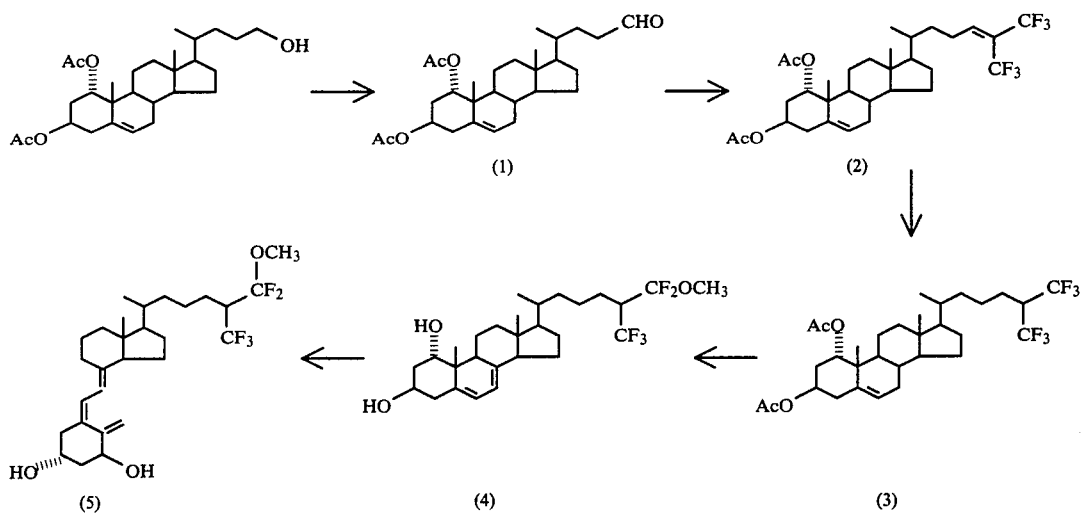

UV-irradiation and pentafluoro-1α-hydroxy-27-methyoxyvitamin D₃ (5) was recovered.

SYNTHESIS

The physico-chemical data set forth in the following detailed description of the synthesis of the compounds of this invention were obtained as indicated below.

Melting points were determined on a hot stage microscope and were uncorrected. U.V. spectra were obtained in ethanol solution with a Shimadzu UV-200 double beam spectrophotometer. IR spectra were taken with a JEOL IRA-1 diffraction grating infrared spectrophotometer. $^1$H-NMR spectra were run on a Varian EM-390 spectrometer for solutions in CDCl$_3$ unless otherwise stated, with tetramethylsilane as an internal reference. $^{19}$F-NMR spectra were recorded on a Varian EM-360L spectrometer in CDCl$_3$ solution, with benzotrifluoride as an internal reference (a plus means high field). Mass spectra were obtained with a HITACHI double focusing mass spectrometer RMU-7L. Column chromatography was effected with silica gel (Merck, 70-23 mesh). Preparative thin layer chromatography was carried out on precoated plates of silica gel (Merck, silica gel 60 F$_{254}$). The usual work-up refers to dilution with water, extraction with an organic solvent, washing to neutrality, drying over magnesium sulfate, filtration, and removal of the solvent under reduced pressure. The following abbreviations were used: THF, tetrahydrofuran; ether, diethyl ether; HMPA, hexamethylphosphoramide; TsOH, p-toluenesulfonic acid; THP, tetraphdropyranyl; s, singlet; d, doublet; t, triplet; q, quatraplet; m, multiplet; bs, broaden singlet. All temperates are in °C.

1α,3β-Diacetoxychol-5-en-24-ol (1)

To a solution of oxalyl chloride (0.32 ml, 3.69 mmol) in dichloro-methane (12 ml) was added dimethylsulfoxide (0.52 ml, 7.38 mmol) at −78° under Argon atmosphere and the mixture was stirred at 78° for 10 min. Then 1α,3β-diacetoxychol-5-en-24-ol (Chem. Pharm. Bull., 30, 4297 (1982) (850 mg, 1.85 mmol) in dichloromethane (7 ml) was added and the solution was further stirred. After 15 min, triethylamine (2.05 ml, 14.76 mmol) was added and the mixture was stirred for 5 min, then warmed to room temperature. The usual work-up (ether) gave a crude product, which was chromatographed on silica gel (74 g). Elution with hexane-ethyl acetate (4:1) gave the aldehyde (1) (750 mg, 89%), amorphous solid. $^1$H-NMR (CDCl$_3$) δ: 0.65(3H, s, 18-H$_3$), 1.04(3H, S, 19-H$_3$), 1.94(3H, s, acetyl), 1.97(3H, s, acetyl), 4.82(1H, m, 3α-H), 4.95(1H, m, 1β-H), 5.41(1H, m, 6-H), 9.58(1H, t, J=1.6 Hz, 24-H).

It is to be understood that in the foregoing procedure blocking groups other than the acetate group can be utilized in the starting material. For example, acyl groups having from 1 to about 4 carbon atoms can be readily utilized as well as other blocking groups which will be evident to those skilled in the art.

1α-Acetoxy, 26,26,26,27,27,27-hexafluorocholesterol 3β-acetate (3)

To a solution of 1α,3β-diacetoxychol-5-en-22-al (1) (134 mg, 0.29 mmol) and triphenylphosphine (1.024 g, 3.9 mmol) in ether (50 ml) was added 2,2,4,4-tetratris(-trifluoromethyl)-1,3-dithiethane (760 mg, 2.1 mmol) at −78° C. (dry ice-acetone) and the reaction mixture was stirred for 16 hr. After removal of the solvent under reduced pressure, the residue was chromatographed on silica gel (n-hexane-ethyl acetate 5:1) to give a mixture of the hexafluoride (2) and triphenylphosphine sulfide (394 mg, molar ratio 1:1.77), H-nmr(CDCl$_3$) δ 0.68(3H, s, 18-H$_3$), 0.95(3H, d, J=6 Hz, 21-H$_3$), 1.08(3H, s, 19-H$_3$), 2.02(3H, s, acetyl), 2.05(3H, s, Acetyl), 4.95(1H, m, 3-H), 5.β2(1H, m, 1-H), 5.58(1H, m, 6-H), 6.80(1H, m, 24-H).

This mixture (350 mg) was treated with sodium borohydride (100 mg) in THF (15 ml) and t-butanol (7.5 ml) at room temperature for 22 hr. After the usual work-up [ether-ethyl acetate (1:1) for extraction], the extracts were purified on a column of silica gel (40 g) eluted with n-hexane-ethyl acetate (10:1) to give the crude hexafluorocholesterol (3), which was further purified on a column of silica gel (20 g). Elution of n-hexane-ethyl acetate (20:1) provided the pure hexafluorocholesterol derivative (3) (69 mg, 51%) as amorphous. (6): $^1$H-nmr(CDCl$_3$) δ 0.68 (3H, s, 18-H$_3$), 0.92 (3H, d, J=6 Hz, 21-H$_3$), 1.10(3H, s, 19-H$_3$), 2.03(3H, s, acetyl), 2.07(3H, s, acetyl), 5.00(1H, m, 3-H), 5.10(1H, m, 1-H), 5.58(1H, m, 6-H). $^{19}$F-nmr(CDCl$_3$) −3.3 (3F,d, J=10.3 Hz), −4.1(3F, d, J=10.9 Hz). MS m/e 454(M+−2AcOH−HF), 440, 335, 253. High resolution MS calcd. for CH$_{27}$H$_{35}$F$_5$, 454.2656. Found: 454.2539.

26,26,26,27,27-Pentafluoro-1α,3β-dihydroxy-27-methoxycholesta-5,7-diene (4)

A mixture of 26,26,26,27,27,27-hexafluoro-1α,3β-diacetoxycholest-5-ene (3) (26 mg, 0.044 mmol) and N-Bromosuccinimide (11 mg, 0.062 mmol) in carbontetrachloride (2 ml) was refluxed under argon atmosphere for 25 min. After cooling to 0°, the resulting precipitate was filtered off. The filtrate was concentrated below 40° to leave the residue. This in xylene (2 ml) was added dropwise to a refluxing solution of collidine (0.5 ml) and xylene (1.5 ml) and refluxing was continued for 20 min. The usual work-up (ethyl acetate for extraction) gave the crude diene. This in THF (5 ml) was treated with 5% KOH-MeOH (7.5 ml) for 60 min. The usual work up (ethyl acetate for extraction) gave a crude product, which was submitted to preparative TLC (benzene-ethyl acetate, 1:1, developed three times). The band of Rf 0.41 was scraped off and eluted with ethyl acetate. Removal of the solvent provided the 5,7-diene (4.5 mg, 20%); $UV_{Max}^{EtOH}$: 293, 282, 272 nm. MS m/z: 520 (M+), 500, 482, 466, 287, 269, 251, 233. From the mass spectral data, one fluorine at C-27 was exchanged to methoxy group during the hydrolysis procedure with KOH-MeOH.

26,26,26,27,27-Pentafluoro-1α-hydroxy-27-methoxyvitamin $D_3$ (5)

A solution of the 5,7-diene (4) (4.5 mg, 8.86 μmol) in benzene (90 ml) and ethanol (40 ml) was irradiated with a medium pressure mercury lamp through a Vycor filter with ice cooling under argon atmosphere for 5 min. Then, the reaction mixture was refluxed for 1 hr under argon atmosphere. Removal of the solvent under reduced pressure gave a crude product, which was submitted to preparative TLC (benzene-ethyl acetate, 1:1, developed three times). The band of Rf 0.50 was scraped off and eluted with ethyl acetate. Removal of the solvent provided the vitamin $D_3$ analogue (5) (0.67 mg, 15%), UV $\lambda_{Max}^{EtOH}$: 265 nm, $\lambda_{Min}^{EtOH}$ 228 nm; MS m/z: 50(M+ −HF), 482, 466, 3β5, 287, 269, 251, 233, 213, 152, 134. The band of Rf 0.43 was scraped off and eluted with ethyl acetate. Removal of the solvent recovered the 5,7-diene (1.3 mg, 29%).

The 26,26,26,27,27-pentafluoro-1α-hydroxy-27-methoxy-vitamin $D_3$ (5) can, if desired, be readily obtained in crystalline form by crystallization from suitable solvents such as, hexane, ethers and alcohols (absolute or aqueous) and mixtures thereof as will be evident and well known to those skilled in the art.

The 26,26,26,27,27-pentafluoro-1α-hydroxy-27-methoxy-vitamin $D_3$ compound of this invention may be readily administered as sterile parenteral solutions by injection or intravenously or by alimentary canal in the form of oral dosages, or by suppository. Doses of from about 0.1 μg to about 10 μg per day would be effective in obtaining the physiological calcium balance responses described and which are characteristic of vitamin D-like activity, with maintenance doses of about 0.25 μg being suitable.

Dosage form of the compounds can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given the particular dose to be administered to a host will depend upon the specific disease state being treated, the end results being sought in a particular case, as well as other factors known to those skilled in the art in the therapeutic use of such medicinal agents.

BIOLOGICAL ACTIVITY

The biological activity of 26,26,26,27,27-pentafluoro-1α-hydroxy-27-methoxyvitamin $D_3$ was established through appropriate assays as described following:

BONE CALCIUM MOBILIZATION

Weanling male rats (Holtzman Co., Madison, Wis.) were fed a low calcium vitamin D deficient diet (Suda et al, J. Nutrition (1970) 100, 1049) for three weeks. At the end of that time they were divided into three groups, one of which was given 650 pmols of 1α-hydroxyvitamin $D_3$ (1α-OHD$_3$) dissolved in 0.05 ml of 95% EtOH, one of which was given 650 pmols of 1α-hydroxy-26,26,26,27,27-pentafluoro-27-methoxy vitamin $D_3$ (1αOH-26,26,26,27,27-F$_5$-27OCH$_3$-D$_3$) in the same vehicle as the 1α-hydroxy vitamin $D_3$ and the last of which was given the vehicle alone. The administrations were made intrajugularly 16 hours prior to sacrifice. The blood was collected and centrifuged to obtain the serum. 0.1 ml of serum in each case was mixed with lanthanum chloride solution and the calcium concentration was measured with an atomic absorption spectrophotometer (Perkin-Elmer Model 214). Since intake of calcium from the diet is negligibly low, the increase in serum calcium concentration reflects the bone mobilization activity of the compounds tested. Results are shown in Table I below:

TABLE I

Increase of serum calcium concentration in response to 1αOHD$_3$ or 1αOH—26,26,26,27,27-F$_5$—27-OCH$_3$—D$_3$

| Compound given | Serum calcium (mg/100 ml) | No. of rats |
|---|---|---|
| Vehicle | 3.2 ± 0.1 a* | 4 |
| 1αOHD$_3$ | 4.7 ± 0.5 b | 5 |
| 1αOH—26,26,26,27,27-F$_5$—27-OCH$_3$—D$_3$ | 3.6 ± 0.1 c | 6 |

*Standard deviation of the mean
b & c from a, and b from c significantly different p0.001

RECEPTOR BINDING

Displacement of radiolabeled 1,25-dihydroxy vitamin $D_3$ (1,25-(OH)$_2$D$_3$) from the chick intestinal receptor was measured for 1α-OHD$_3$ and 1αOH-26,26,26,27,27-F$_5$-27-OCH$_3$-D$_3$ in accordance with the method of Shepard et al (Biochem. J. (1978) 182, 55–69). The results obtained, which are shown in FIG. 1, demonstrate that the pentafluoro compound is about three times more potent than 1α-OHD$_3$ in displacing radiolabeled 1,25-(OH)$_2$D$_3$ from the receptor, which is evidence of the vitamin D-like activity of these compounds in calcium intestinal transport and bone mineralization.

We claim:
1. Compounds having the formula

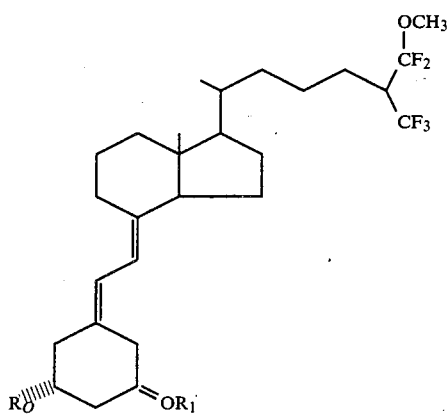

where R and R₁ are selected from the group consisting of hydrogen and an acyl group having from 1 to about 4 carbon atoms.

2. The compounds of claim 1 in crystalline form.

3. A pharmaceutical composition comprising at least one compound of claim 1 together with at least one pharmaceutically acceptable excipient.

4. 26,26,26,27,27-pentafluoro-1α-hydroxy-27-methoxy-vitamin $D_3$.

5. A pharmaceutical composition comprising the compound of claim 4 together with at least one pharmaceutically acceptable excipient.

6. The compound of claim 4 in crystalline form.

7. Compounds having the formula

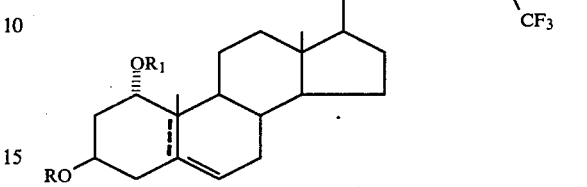

where R and R₁ are selected from the group consisting of hydrogen and an alkyl group having from 1 to about 4 carbon atoms $R_2$ is selected from the group consisting of hydrogen and —$OCH_3$ and the dotted line represents a carbon to carbon bond when $R_2$ is —$OCH_3$.

8. 1α,3β-dihydroxy-26,26,26,27,27-pentafluoro-27-methoxy-cholesta-5,7-diene.

* * * * *